(12) United States Patent
Bettman et al.

(10) Patent No.: US 6,344,215 B1
(45) Date of Patent: Feb. 5, 2002

(54) METHYLPHENIDATE MODIFIED RELEASE FORMULATIONS

(75) Inventors: Marie J. Bettman, Clayton; Phillip J. Percel, Troy; Dan L. Hensley, Huber Heights; Krishna S. Vishnupad; Gopi M. Venkatesh, both of Dayton, all of OH (US)

(73) Assignee: Eurand America, Inc., Vandalia, OH (US)

( * ) Notice: Subject to any disclaimer, the term of this patent is extended or adjusted under 35 U.S.C. 154(b) by 0 days.

(21) Appl. No.: 09/697,803

(22) Filed: Oct. 27, 2000

(51) Int. Cl.⁷ .............................. A61K 9/56; A61K 9/54; A61K 9/58; A61K 9/22; A61K 31/21
(52) U.S. Cl. ..................... 424/459; 424/458; 424/462; 424/468; 424/457; 424/451
(58) Field of Search .................................. 424/451, 457, 424/458, 459, 462, 468

(56) References Cited

U.S. PATENT DOCUMENTS

| | | | |
|---|---|---|---|
| 3,184,386 A | 5/1965 | Stephenson | 167/82 |
| 3,558,768 A | 1/1971 | Klippel | 424/21 |
| 4,752,470 A | 6/1988 | Mehta | 424/458 |
| 4,840,799 A | 6/1989 | Applegren et al. | 424/493 |
| 4,892,741 A | 1/1990 | Ohm et al. | 424/479 |
| 5,133,974 A | 7/1992 | Paradissis et al. | 424/480 |
| 5,837,284 A | * 11/1998 | Mehta et al. | 424/459 |
| 6,024,982 A | 2/2000 | Oshlack et al. | 424/476 |

* cited by examiner

Primary Examiner—Thurman K. Page
Assistant Examiner—Rachel M. Bennett
(74) Attorney, Agent, or Firm—Thompson Hine LLP

(57) ABSTRACT

A pharmaceutical MR (modified release) multiparticulate dosage form such as a capsule (once-a-day MR Capsule) of Methylphenidate indicated for the treatment of children with attention deficit hyperactivity disorder (ADHD), capable of delivering a portion of the dose for rapid onset of action and the remainder of the dose in a controlled manner for about 12 hours, is composed of a multitude of multicoated particles made of two populations of drug layered beads, IR (immediate release) and ER (extended release) Beads. The IR beads preferably are made by layering an aqueous solution comprising a drug and a binder on to non-pareil sugar spheres and then applying a seal coat to the drug coated cores. The ER Beads are made by applying an extended release coating of a water insoluble dissolution rate controlling polymer such as ethylcellulose to IR Beads. The MR Capsules are manufactured by filling IR and ER Beads in a proper ratio; the dose and the ratio required for an efficacious, cost effective and patient compliant treatment of children with ADHD were determined from extensive clinical investigations and in vitro- in vivo correlations performed as per FDA Guidelines, Guidance for Industry: Extended Release Oral Dosage Forms.

9 Claims, 4 Drawing Sheets

METHYLPHENIDATE MODIFIED RELEASE FORMULATIONS

BACKGROUND OF THE INVENTION

Methylphenidate Hydrochloride, a scheduled II controlled substance, is currently marketed as a mild central nervous system (CNS) stimulant and the drug of choice for treatment of ADD and ADHA in children. The drug is well absorbed throughout the gastrointestinal tract. However, it has an extremely short half-life, which necessitates a multi-dose treatment regimen for conventional (immediate release) dosage forms such as currently available 5, 10, and 20 mg tablets. Due to high $C_{max}$, oral administration of 10 and 20 mg Ritalin® is reported to result in notable side effects such as anorexia, weight loss, dizziness, etc. Furthermore, it requires the hyperactive children to be dosed in school thus causing hardship to school authorities as well as parents. The drawback of methylphenidate is that it also produces a euphoric effect when administered intravenously or through inhalation, thus presenting a high potential for substance abuse. Sustained release formulations for once-a-day dosing, such as 20 mg Ritalin SR® tablets currently available from Novartis and Geneva (generic version), were developed with the objective of providing efficacy for 8 hours, thereby improving compliance and reducing the incidence of diversion. However, there are reports which strongly suggest that the sustained release formulations exhibit a slower onset of action/efficacy compared to the immediate release dosage forms (W.E. Pelham et al., "Sustained Release And Standard Methylphenidate Effects On Cognitive And Social Behavior In Children With Attention Deficit Disorder," Pediatrics, Vol. 80, pp 491–501 (1987)).

Recently, OROS® (methylphenidate HCl) has been approved by FDA. It is a new osmotic controlled release once-a-day oral dosage form with a drug overcoat, that is designed to deliver a portion of the dose for rapid onset of action and deliver the remainder of the dose in a controlled manner for about 10 hours. The manufacturing cost of this complicated dosage form is expected to be very high and hence resulting in a high cost of treatment. Hence, there is a dire need to develop modified release dosage forms with moderate cost of goods and having not only a rapid onset of action but also with a significantly longer duration of action.

U.S. Pat. No. 5,908,850 assigned to Celgene Corporation discloses a method for treating children with the above disability to be treated using a sustained release dosage form containing d-threo-methylphenidate or pharmaceutically acceptable salts thereof thus minimizing hyperactivity and side effects. However, it does not address how it avoids dosing in school, thereby minimizing potential drug abuse.

It has been amply demonstrated that by administering two-bead capsule dosage forms manufactured in accordance with the present invention, therapeutically efficacious plasma concentrations can be achieved for rapid onset of action and maintained for over a 12-hour period, thus eliminating the need to dose children in the school.

SUMMARY OF THE INVENTION

An object of the present invention is to provide a method for manufacturing pharmaceutically elegant multi-particulate dosage forms based on the Difficaps® technology, having two types of bead populations—one immediate release (IR) Bead and the other extended release (ER) Bead. The IR Bead is designed to release all of the dose over a short period of time, preferably within 30 minutes to act as a bolus dose for rapid onset of action. In contrast, the ER Bead is designed to release the remainder of the total dose as a desired profile over a 12-hour period when dissolution tested in water by USP Apparatus 2 (Paddles @ 50 rpm). Testing to determine in vitro/in vivo correlations can be conducted to predict desirable profiles which can be expected to maintain blood levels of the active agent within a desired therapeutic range over an extended period of time. Another objective is to provide a novel multi-particulate dosage form in order to minimize side effects and eliminate the need to dose children with ADD and ADHD in the school, the release rates from ER Beads and the ratio of IR to ER Beads being determined based on the in vitro/in vivo correlations and efficacy study results obtained.

DETAILED DESCRIPTION OF THE INVENTION

Figure 1:
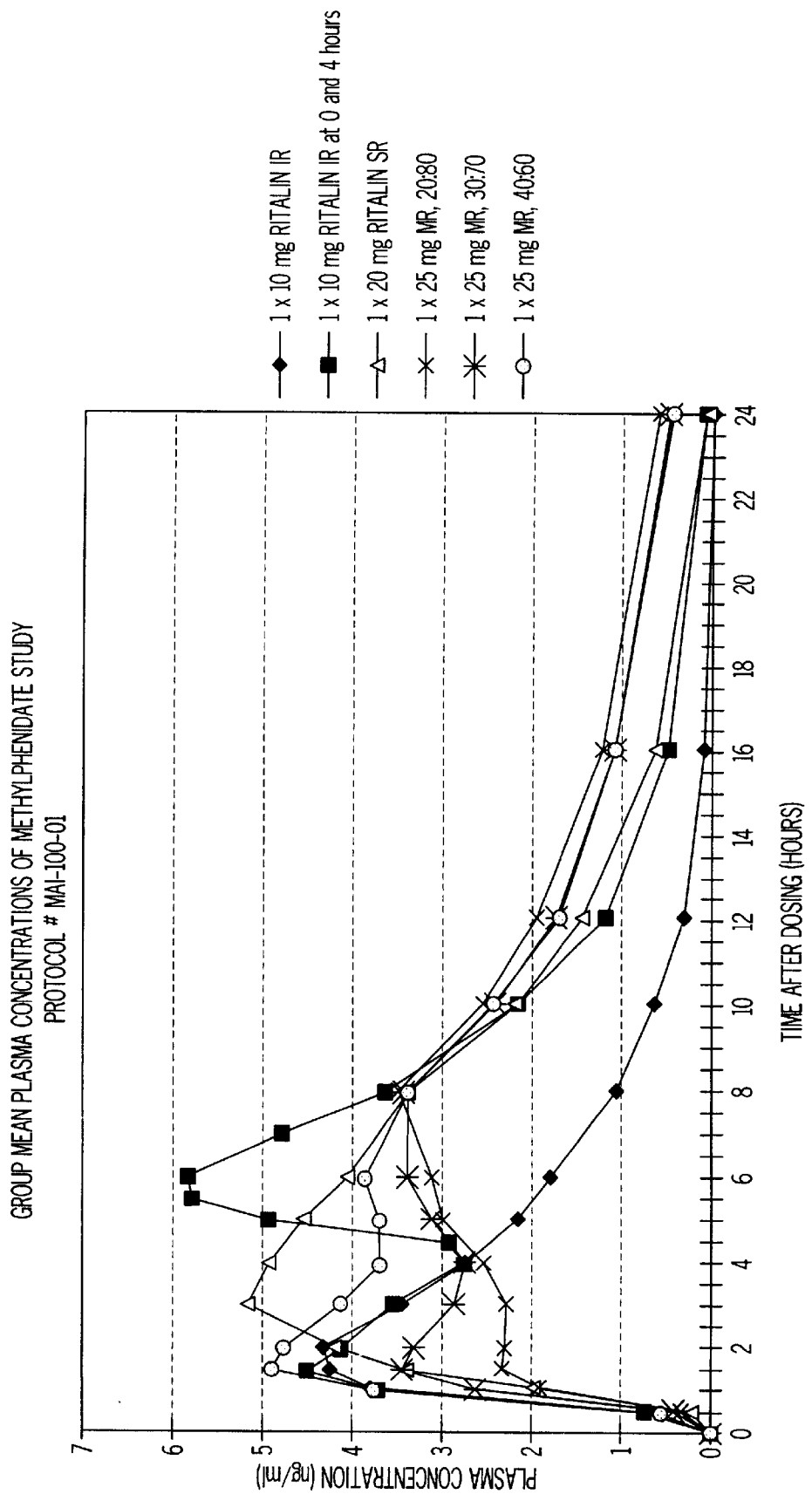
FIG. 1 is a graph showing the mean plasma concentration profile for various dosage forms described in example 2.

The active core of the novel dosage form of the present invention may be comprised of an inert particle such as a commercially available non-pareil sugar sphere. Methylphenidate is layered on the sugar spheres from an aqueous solution of the drug and a binder such as polyvinylpyrrolidone (PVP). "Methylphenidate" as used herein includes all optical isomers of the compound and all pharmaceutically acceptable salts thereof. The drug layered beads are provided with up to 4%, preferably up to 2% w/w seal coat using a film-former, such as hydroxypropylmethylcellulose (HPMC) (e.g., Opadry Clear) to produce IR Beads.

ER Beads are produced by coating IR Beads with a solution or an aqueous dispersion of a dissolution rate controlling polymer thereby forming an extended release membrane coating on the IR bead. Examples of dissolution rate controlling polymers include, but are not limited to, ethylcellulose (e.g., Aquacoat® ECD-30), neutral copolymers based on ethylacrylate and methylmethacrylate, and copolymers of acrylic and methacrylic acid esters having quaternary ammonium groups. The membrane coated beads are also typically seal coated with HPMC to produce Extended Release (ER) Beads. The IR and ER Beads are filled into hard gelatin capsules at predetermined ratios to produce modified release (MR) Beads. Ratios found to provide desirable release profiles ranges from about 10IR/90ER to 50IR/50ER, preferably from 20IR/80ER to 40IR/60ER, and most preferably at a ratio of 30IR/70ER.

The amount of drug layered on the core (sugar sphere) can be varied widely. A typical dose is expected to be from about 10 to 40 mg of active drug. IR beads typically will account for about 20 to 40% of the dose. Due to limitations in accurately dosing small fill weights into capsules in a two-bead capsule filling equipment, the drug content in the drug layered beads may range from 5 to 20% w/w. Those skilled in the art will be able to select an appropriate amount of drug for coating onto the core to achieve the desired dosage. Generally, the dissolution rate controlling polymeric coatings on the active core particle vary from 5 to 25%, preferably from 5 to 20% and more preferably from 5 to 10% by weight based on the total weight of the coated particle, depending on the coating materials and solvents selected.

The thickness of the membrane layer or the type of polymer selected depends on the desired release profile, and is optimized for achieving a desired in vitro release profile, which is predicted based on the in vitro/in vivo correlations and efficacy study results. Preferably, the release profile provides an immediate bolus of drug and extended release of the drug at a relatively constant rate for an extended period of time (over 12 hours or more). The unit dosage form according to the present invention may comprise one bead population, which provides only an extended release profile. Alternately, it may consist of an IR bead population that provides a short-duration (sustained release) bolus component of the dose by optionally coating IR Beads with a mixture of water insoluble and water soluble polymers at a ratio of 95/5 to 70/30.

The invention also provides a method of manufacturing a modified release methylphenidate dosage form having a mixture of two bead populations which comprises the steps of:

1. coating an inert particle such as a non-pareil seed with methylphenidate and a polymeric binder to form IR Beads, which may be present in the unit dosage form to act as a bolus dose;
2. coating said particle with a plasticized solution or suspension of a water insoluble polymer or a mixture of water soluble and water insoluble polymers and curing at high temperatures (e.g., 50°–70° C.) for 4 to 12 hours, to form extended release (ER) Beads; and
3. filling into hard gelatin capsules beads of (1) and/or (2) at a ratio of 20 IR/80 SR to 40 IR/60 SR Beads, each capsule containing 10 to 40 mg methylphenidate hydrochloride.

An aqueous or a pharmaceutically acceptable solvent medium may be used for preparing drug containing core particles. The type of film forming binder that is used to bind the water soluble drug to the inert sugar sphere is not critical but usually water soluble, alcohol soluble or acetone/water soluble binders are used. Binders such as polyvinylpyrrolidone (PVP), polyethylene oxide, hydroxypropyl methylcellulose (HPMC), hydroxypropyl cellulose (HPC), polysaccharides such as dextran, corn starch may be used at concentrations of 0.5 to 5 weight %. The drug substance may be present in this coating formulation up to 55 weight %, preferably up to about 40% weight %, and most preferably up to about 20% weight, depending on the viscosity of the coating formulation.

Dissolution rate controlling polymers suitable for incorporating in the formulation for producing ER Beads are selected from the group consisting of ethylcellulose (or e.g., Aquacoat® ECD-30), neutral copolymers based on ethylacrylate and methylmethacrylate, copolymers of acrylic and methacrylic acid esters having quaternary ammonium groups, polyvinyl acetate/crotonic acid copolymer and combinations thereof.

Dissolution rate controlling polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof.

The plasticizer may comprise about 3 to 30 wt. % and more typically about 10 to 25 wt. % based on the polymer. The plasticizer is selected based on the total solids in the coating system (dissolved or dispersed) and depends on the polymer or polymers and the nature of the coating medium. Generally, this will be between 5 and 40 weight percent based on the total weight of the coating system.

The release characteristics of the IR Beads can optionally be further modified to provide a short duration (sustained release) bolus dose. The IR Beads in this embodiment are coated with a mixture of a water insoluble polymer such as ethylcellulose and a water soluble polymer such as low molecular weight HPMC, HPC, methylcellulose, polyethylene glycol (PEG) at a thickness of from 1 weight % up to 5 weight % depending on the solvent or latex dispersion based coating formulation used. The water insoluble polymer to water soluble polymer ratio may typically vary from 95:5 to 70:30.

The following non-limiting examples illustrate the dosage formulations in accordance with the invention.

EXAMPLES

Modified Release (MR) Capsules of Methylphenidate Hydrochloride, a ADD or ADHD drug, consist of a mixture of two sets of beads: The first set is referred to as immediate release (IR) Beads. IR Beads are designed to provide a loading or bolus dose by releasing all of the methylphenidate hydrochloride within the first hour, preferably within the first 30 minutes. The second set is referred to as the Extended Release (ER) Beads. ER Beads are designed to release methylphenidate slowly over a period of 10–12 hours.

In a preferred embodiment, IR Beads are prepared by adding methylphenidate HCl to an aqueous binder solution, preferably a PVP solution. Sugar spheres are coated with the drug solution and then dried. The drug containing particles are coated with a sealcoat of HPMC (Opadry Clear) to form IR Beads in accordance with the invention. Release characteristics of the IR Beads can be modified by optionally coating IR Beads with a blend of a water soluble polymer such as HPMC and a water insoluble polymer such as ethylcellulose.

The ER Beads are produced by applying a layer of extended release membrane coating (with a dissolution rate controlling polymer such as ethylcellulose) and then a seal coat on IR Beads. The two sets of beads when filled into capsule shells at an appropriate ratio will produce the target in vitro release profile which in turn will result in plasma concentrations required to provide rapid onset of action and efficacy over several hours in school going children with ADD or ADHD.

Example 1

Methylphenidate HCl (200 g) was slowly added to an aqueous solution (about 15% solids) of polyvinylpyrrolidone (10 g Povidone K-30) and mixed well. 25–30 mesh sugar spheres (770 g) were coated with the drug solution in a Versa Glatt fluid bed granulator. The drug containing pellets were dried, and a sealcoat of Opadry Clear (20 g) was first applied to produce IR Beads. ER Beads are produced by taking IR Beads and coating with the dissolution rate controlling polymer. A plasticized ethylcellulose coating was applied to the methylphenidate particles (893 g) by spraying Aquacoat® ECD-30 (233 g) and dibutyl sebacate (16.8 g). An outer seal coating formulation (20 g) of Opadry was sprayed onto the coated active particles. The coated particles were cured at 60° C. for 12 hours so that polymer particles coalesce to form a smooth membrane on ER Beads.

The IR and ER Beads were then filled into hard gelatin capsules using an MG Capsule Filling Machine with dual bead filling hoppers. Three clinical batches, Methylphenidate HCl MR Capsules, 25 mg (20 IR/80 ER Beads), 25 mg (30 IR/70 ER Beads) and 25 mg (40 IR/60 ER Beads), were manufactured, tested, and released for pilot biostudies. The dissolution profiles of these capsules are presented in Table 1 showing increasing release rates with increasing IR Bead fraction in the finished capsule.

TABLE 1

Dissolution Data for Example 1

| Time, hours | (20 IR/80 ER Beads) | (30 IR/70 ER Beads) | (40:IR/60 ER Beads) |
|---|---|---|---|
| 0.0 | 0.0 | 0.0 | 0.0 |
| 1.0 | 24.5% | 31.6% | 42.1% |
| 2.0 | 29.8% | 37.4% | 48.3% |
| 4.0 | 57.8% | 59.0% | 66.3% |
| 8.0 | 79.2% | 76.3% | 83.5% |
| 12.0 | 89.1% | 84.6% | 88.2% |

Example 2

In order to evaluate the bioavailability of the pilot clinical supplies manufactured as described in Example 1 and to establish in vitro-in vivo correlations, a randomized, open-labelled, six-period crossover biostudy was conducted in 24 healthy subjects, of which 18 subjects completed the study. Treatment regimens included a single oral dose of (A) one 10 mg Ritalin® IR tablet, (B) one 10 mg Ritalin IR tablet at 0 and 4 hours, (C) one 20 mg Ritalin® SR tablet, (D) one 25 mg MR Capsule (20 IR/80 ER Beads), (E) one 25 mg MR Capsule (30 IR/70 ER Beads), and (F) one 25 mg MR Capsule (40 IR/60 ER Beads). Pharmacokinetic assessments were made by measuring serial plasma methylphenidate concentrations after administration of each formulation. Each of the treatments administered resulted in a unique mean plasma concentration profile (FIG. 1). Treatments A, B, and C appeared to have similar elimination rate processes. In contrast, treatments D, E, and F appeared to have similar but slower elimination rate processes, implying that the methylphenidate elimination rate following the administration of Treatments D, E, and F is limited by the release rate from the MR capsule. Based on the study results, the Treatment F met the bioequivalence confidence interval requirements with Treatment C, the 20 mg methylphenidate SR formulation, suggesting the need for a faster release rate from the dosage form manufactured in accordance with the present invention.

Example 3

Methylphenidate HCl (1,168.4 g) was slowly added to a solution of polyvinylpyrrolidone (58.4 g Povidone K-30) in 7,536 g of purified water and mixed well. 25–30 mesh sugar spheres (4,500 g) were coated with the drug solution in a Glatt fluid bed granulator GPCG 5. The drug containing pellets were dried, and a sealcoat of Opadry Clear (121.7 g) in 1,400 g purified water was first applied. The dissolution rate controlling polymer coating was applied to the active particles (4,500 g) by spraying a dispersion of Aquacoat ECD (1,187.4 g) and dibutyl sebacate (85.5 g) in 199.5 g purified water. An outer seal coating formulation (Opadry) (101.8 g) in 1,170.7 g purified water was sprayed onto the coated active particles. The coated particles were cured at 60° C. for 12 hours so that the polymers were coalesced to produce ER Beads.

An IR Bead batch (Batchsize: 5,535.6 g) at 10% drug load was also prepared by following the above procedure. Methylphenidate MR Capsules, 20 mg (30 IR/70 ER) Batch (6000 size #3 capsules), containing 6.0 mg of IR Beads and 14 mg of ER Beads were manufactured using MG2 Futura capsule filling equipment. Similarly, Methylphenidate HCl MR Capsules, 20 mg (40 IR/60 ER Beads) Batch, were manufactured.

TABLE 2

Dissolution Data for Example 3

| Time, hours | (30 IR/70 ER Beads) | (40 IR/60 ER Beads) |
|---|---|---|
| 0.0 | 0.0 | 0.0 |
| 1.0 | 33.4% | 41.3% |
| 2.0 | 44.9% | 50.9% |
| 4.0 | 66.2% | 69.6% |
| 8.0 | 87.1% | 89.2% |
| 12.0 | 97.1% | 98.0% |

Example 4

Figure 2:
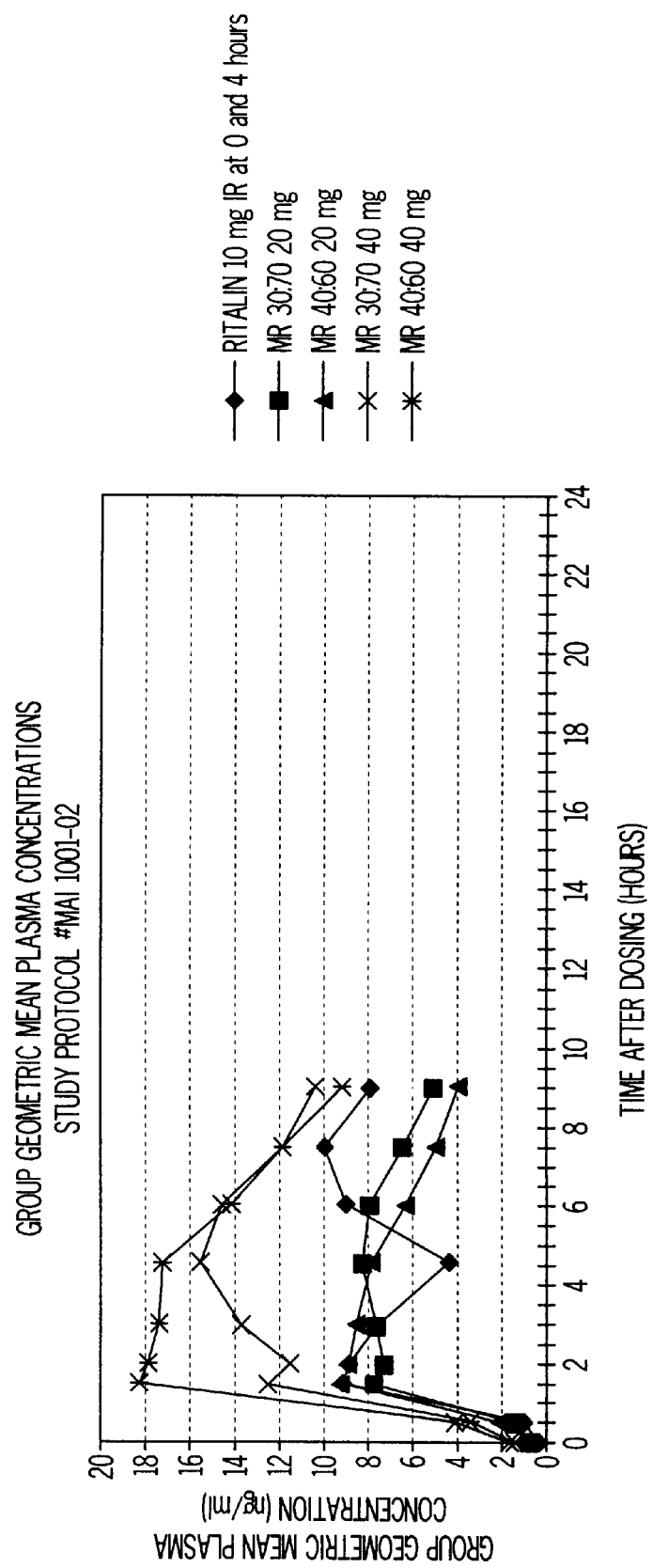
FIG. 2 is a graph showing the mean methylphenidate plasma concentrations versus time profiles for the dosage forms described in example 4.

A randomized six-way crossover study in 24 healthy children with ADHD (Protocol MAI 1001-02) was performed using 20 mg MR Capsules (30 IR/70 ER Beads and 40 IR/60 ER Beads of Example 3) and 2×20 mg dosed to children in the fed condition in comparison with Ritalin IR 10 mg dosed twice. The plasma profiles were obtained in a randomized, two-double-blind, crossover comparison of IR bid and placebo in stage 1 and two doses of two MR capsules in stage 2 in 24 healthy children. Children received MR capsules (30 IR/70 ER and 40 IR/60 ER Beads of Example 3, single and double doses) and one dosing regimen of Ritalin IR tablets (10 mg bid). Mean methylphenidate Plasma concentrations versus Time profiles are presented in FIG. 2. A level A correlation was established between the in vitro release and in vivo absorption with a correlation coefficient of $r^2=0.98$ and a slope of almost 1, as per the FDA guidelines, Guidance for Industry: Extended Release Oral Dosage Forms.

Example 5

Methylphenidate HCl (11.7 kg) was slowly added to an aqueous solution of polyvinylpyrrolidone (500 g Povidone K-30) and mixed well. 25–30 mesh sugar spheres (38.5 kg) were coated with the drug solution in a fluid bed equipment, Fluid Air FA 0300. The drug containing pellets were dried, and a sealcoat of Opadry Clear (2% w/w) in purified water was first applied. The dissolution rate controlling polymer coating was applied to the active particles (8.6% w/w) by spraying a dispersion of Aquacoat ECD and dibutyl sebacate. An outer seal coat of Opadry Clear (2% w/w) was applied onto the coated active particles. The coated particles were cured at 60° C. for 12 hours so that the polymers were coalesced to produce ER Beads. An IR Bead batch (Batchsize:50.4 kg) at about 10% drug load was also prepared by following the above procedure. Methylphenidate MR Capsules, 20 mg in size #3 capsules, containing 6.0 mg of IR Beads and 14 mg of ER Beads were manufactured using an MG Futura capsule filling equipment. Similarly, Methylphenidate HCl MR Capsules, 10 mg (30 IR/70 ER Beads) and 30 mg (30 IR/70 ER Beads), were also manufactured. The initial and up to 18-month stability data at 30°

Figure 3:
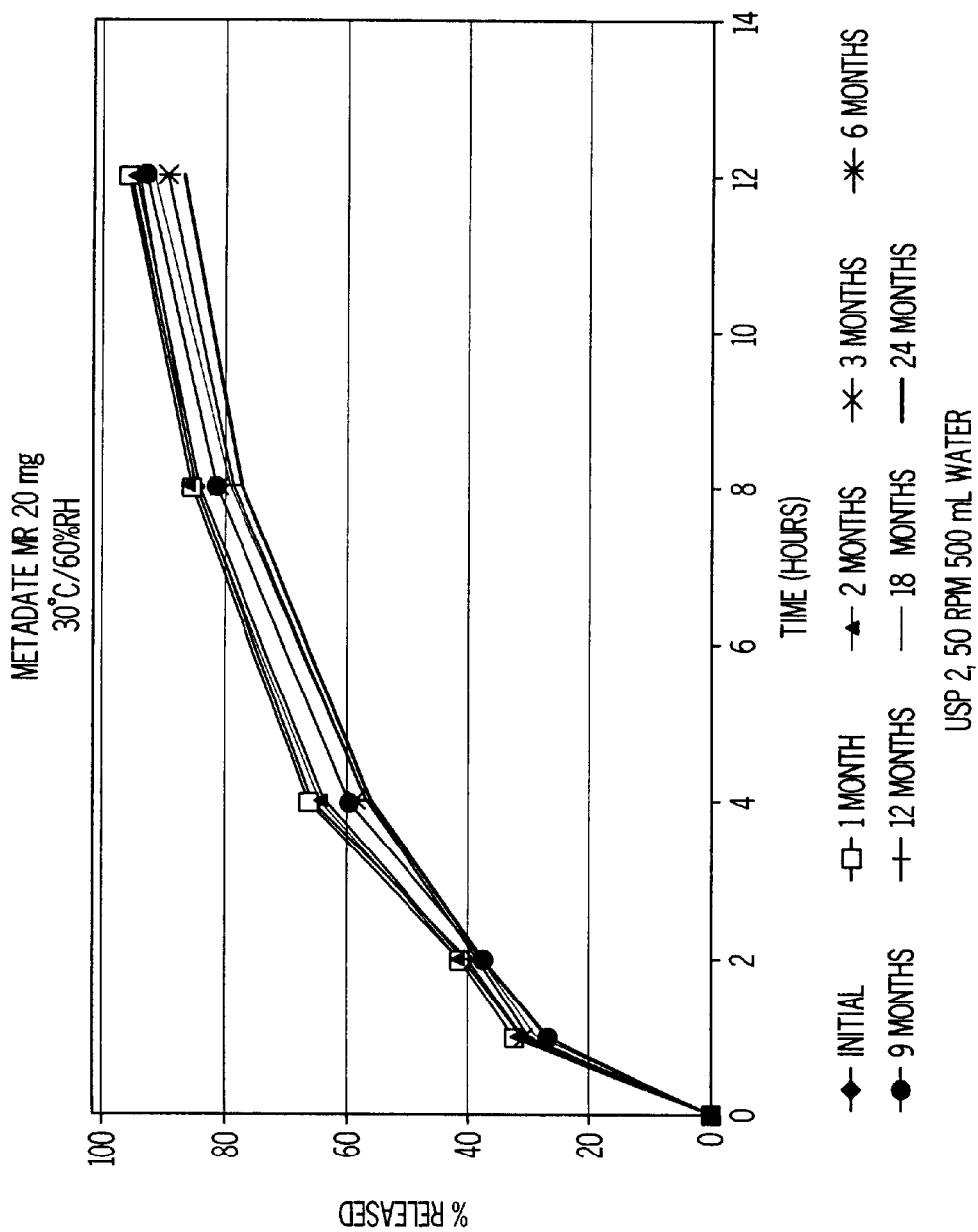
FIG. 3 is a graphical representation of the stability data for modified release methylphenidate hydrochloride capsules, 20 mg (30 IR/70 ER Beads) at 30° C./60% RH.
Figure 4:
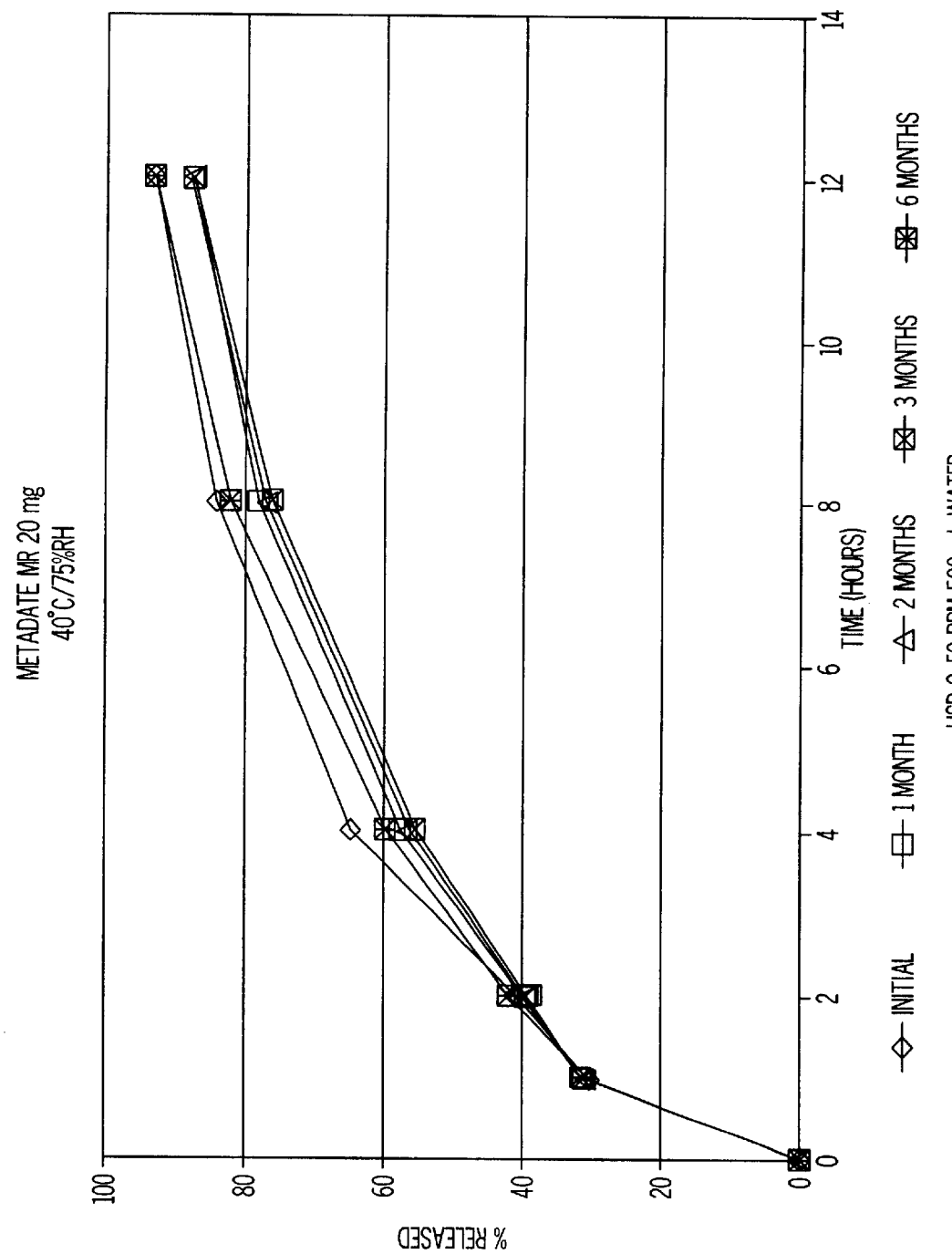
FIG. 4 is a graphical representation of the stability data for modified release methyphenidate hydrochloride capsules, 20 mg (30 IR/70 ER Beads) at 40° C./75% RH.

C./60% RH and up to 6-month stability data at 40° C./75% RH for MR Capsules, 20 mg, are presented, respectively, in FIGS. 3 and 4. Both 10 and 30 mg capsule products at the ratio of 30 IR/70 ER Beads have also demonstrated to be physically and chemically stable.

Example 6

Methylphenidate HCl (2,336.8 g) was slowly added to an aqueous solution of polyvinylpyrrolidone (116.8 g Povidone K-30) in 14,072 g of purified water and mixed well. 25–30 mesh sugar spheres (9,000 g) were coated with the drug solution in a Glatt fluid bed granulator GPCG 5. The drug containing pellets were dried, and a sealcoat of Opadry Clear (243.4 g) in 2,800 g purified water was first applied. The dissolution rate controlling polymer coating was applied to the active particles (9,500 g) by spraying a solution of ethylcellulose and diethyl phthalate in 98/2 acetone/water. The coated ER Beads were cured at 60° C. for 4 hours. IR Beads were prepared by following above procedure. The IR and ER Beads were filled into capsules at a ratio of 30 IR/70 ER Beads.

While the invention has been described in detail with respect to specific embodiments thereof, it will be apparent that numerous modifications and variations are possible without departing from the scope of the invention as defined by the following claims.

What is claimed is:

1. A modified release methylphenidate hydrochloride capsule comprising immediate release (IR) and extended release (ER) methylphenidate-containing beads wherein the immediate release beads are present in an amount of about 20 to 40 percent and the extended release beads are present in an amount of about 60 to 80 percent and the total amount of methylphenidate hydrochloride present is about 10 to 40 mg; further wherein the immediate release beads are made up of a core particle coated with a layer of a methylphenidate-containing water soluble film-forming composition and the extended release beads are made up of a core particle layered with a methylphenidate-containing water soluble film-forming composition which is further coated with a dissolution rate controlling polymer in an amount up to 20 percent, and when the immediate release and the extended release beads are mixed in the amounts shown in the following table and tested using USP apparatus 2 at 50 rpm in 500 ml water, the mixed beads release methylphenidate approximately in the percentages shown in the following table based on the total methylphenidate:

| Time, hours | (20 IR/80 ER Beads) | (30 IR/70 ER Beads) | (40 IR/60 ER Beads) | (30 IR/70 ER Beads) | (40 IR/60 ER Beads) |
| --- | --- | --- | --- | --- | --- |
| 0.0 | 0.0 | 0.0 | 0.0 | 0.0 | 0.0 |
| 1.0 | 24.5% | 31.6% | 42.1% | 33.4% | 41.3% |
| 2.0 | 29.8% | 37.4% | 48.3% | 44.9% | 50.9% |
| 4.0 | 57.8% | 59.0% | 66.3% | 66.2% | 69.6% |
| 8.0 | 79.2% | 76.3% | 83.5% | 87.1% | 89.2% |
| 12.0 | 89.1% | 84.6% | 88.2% | 97.1% | 98.0% |

2. The capsule of claim 1 wherein the dissolution rate controlling polymer is ethylcellulose.

3. The capsule of claim 2 wherein the methylphenidate containing film-forming composition is a composition of polyvinylpyrrolidone.

4. The capsule of claim 3 wherein, when mixed in the amount shown in the following table, the immediate release and the extended release beads release the methylphenidate in the percentages shown in the following table.

| Time, hours | (30 IR/70 ER Beads) | (40 IR/60 ER Beads) |
| --- | --- | --- |
| 0.0 | 0.0 | 0.0 |
| 1.0 | 33.4% | 41.3% |
| 2.0 | 44.9% | 50.9% |
| 4.0 | 66.2% | 69.6% |
| 8.0 | 87.1% | 89.2% |
| 12.0 | 97.1% | 98.0% |

5. The capsule of claim 4 wherein the dissolution rate controlling polymer is a plasticized dissolution rate controlling water insoluble ethylcellulose formulation wherein the plasticizer is selected from the group of dibutyl sebacate, triethyl citrate, diethyl phthalate, tributyl citrate, triacetin and mixtures thereof.

6. The capsule of claim 5 wherein the immediate release and extended release beads are further coated with a seal coat in an amount up to about 4%.

7. The capsule of claim 6 wherein the seal coat is hydroxypropylmethylcellulose.

8. The capsule of claim 1 wherein the immediate release and extended release beads are mixed in the ratios shown in the table in claim 1 and release methylphenidate approximately in the percentages shown in the table in claim 1.

9. The capsule of claim 4 wherein the immediate release and extended release beads are mixed in the ratios shown in the table in claim 4 and release methylphenidate approximately in the percentages shown in the table in claim 4.

* * * * *